United States Patent
Burk et al.

(10) Patent No.: US 9,981,938 B2
(45) Date of Patent: May 29, 2018

(54) QUATERNARY AMMONIUM ALKYL ESTERS AS STABLE PRODRUGS

(71) Applicant: ALLERGAN, INC., Irvine, CA (US)

(72) Inventors: Robert M. Burk, Laguna Beach, CA (US); David W. Old, Irvine, CA (US); Wha Bin Im, Irvine, CA (US); Richard S. Graham, Irvine, CA (US); Mu-Lan Lee, Tustin, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days. days.

(21) Appl. No.: 15/310,738

(22) PCT Filed: May 12, 2015

(86) PCT No.: PCT/US2015/030395
§ 371 (c)(1),
(2) Date: Nov. 11, 2016

(87) PCT Pub. No.: WO2015/175544
PCT Pub. Date: Nov. 19, 2015

(65) Prior Publication Data
US 2017/0081304 A1    Mar. 23, 2017

Related U.S. Application Data

(60) Provisional application No. 61/991,921, filed on May 12, 2014.

(51) Int. Cl.
| | | |
|---|---|---|
| C07D 333/40 | (2006.01) |
| A61K 31/5575 | (2006.01) |
| A61K 31/381 | (2006.01) |
| A61P 27/06 | (2006.01) |
| A61Q 7/00 | (2006.01) |
| C07D 333/38 | (2006.01) |

(52) U.S. Cl.
CPC ......... *C07D 333/38* (2013.01); *C07D 333/40* (2013.01)

(58) Field of Classification Search
CPC ............................ C07D 333/38; C07D 333/40
See application file for complete search history.

(56) References Cited

U.S. PATENT DOCUMENTS

| | | |
|---|---|---|
| 3,888,905 A | 6/1975 | Miyano |
| 3,980,700 A | 9/1976 | Miyano |
| 7,323,591 B2 | 1/2008 | Old et al. |
| 7,405,240 B2 | 7/2008 | Old et al. |
| 7,635,716 B2 | 12/2009 | Old et al. |
| 7,947,732 B2 * | 5/2011 | Old ...................... C07D 333/16 514/336 |
| 9,573,926 B2 * | 2/2017 | Burk .................... C07D 333/38 |
| 2009/0270396 A1 | 10/2009 | Old et al. |
| 2010/0210689 A1 | 8/2010 | Old et al. |
| 2014/0057975 A1 | 2/2014 | Im et al. |

FOREIGN PATENT DOCUMENTS

| | | |
|---|---|---|
| DE | 2359955 | 6/1975 |
| WO | 2010-111449 | 9/2010 |

OTHER PUBLICATIONS

International Search Report & Written Opinion dated Jul. 14, 2015 for PCT/US15/30395 filed May 12, 2015 in the name of Allergan, Inc.

* cited by examiner

*Primary Examiner* — Amanda L Aguirre
(74) *Attorney, Agent, or Firm* — Jonathan Bass

(57) ABSTRACT

Disclosed herein are compounds according to Formulas 1-12, compositions comprising these compounds, and methods of lowering intraocular pressure (IOP) or causing hair growth, and methods of using the same.

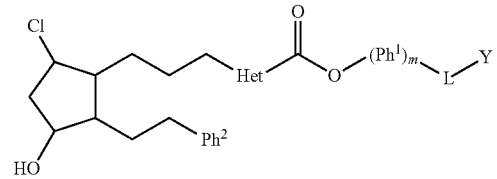

Formula 1

15 Claims, No Drawings

QUATERNARY AMMONIUM ALKYL ESTERS AS STABLE PRODRUGS

CROSS REFERENCE TO RELATED APPLICATIONS

This application is a national stage application under 371 U.S.C. § 371 of PCT Application PCT/US2015/030395 filed May 12, 2015, which claims the benefit of U.S. provisional application 61/991,921 entitled "Quaternary Ammonium Alkyl Esters as Stable Prodrugs" filed on May 12, 2014 which are incorporated herein by reference in their entireties and serve as the basis for a priority claim for the present application.

BACKGROUND

Ocular hypotensive agents are useful in the treatment of a number of various ocular hypertensive conditions, such as post-surgical and post-laser trabeculectomy ocular hypertensive episodes, glaucoma, and as pre-surgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical β-adrenoreceptor antagonists have traditionally been the drugs of choice for treating glaucoma.

SUMMARY

Some embodiments include a compound represented by Formula 1:

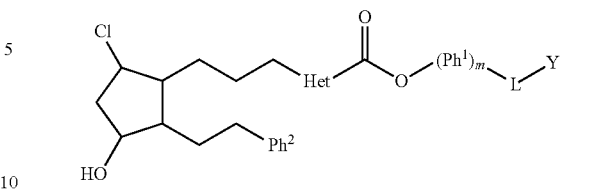

Formula 1 or a pharmaceutically acceptable salt thereof, wherein $Ph^1$ is optionally substituted phenylene, wherein m is 0 or 1; and $Ph^2$ is optionally substituted phenyl; and Het is optionally substituted thienylene; and L is $C_xH_{2x}$, wherein x is 0, 1, 2, 3, 4, or 5; and Y is $C_{1-6}$ alkylamino, $C_{1-6}$ alkylammonium, or optionally substituted morpholino.

Some embodiments include a compound represented by Formula 2:

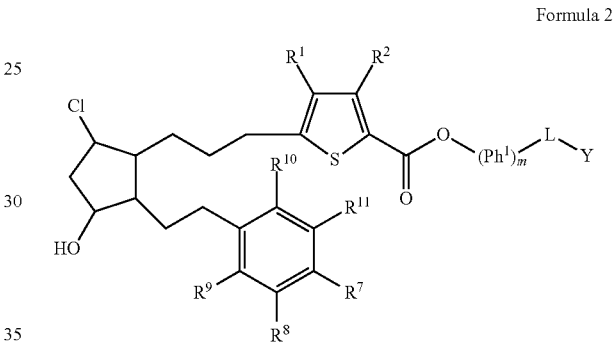

Formula 2 or a pharmaceutically acceptable salt thereof, wherein $Ph^1$ can be optionally substituted phenylene, wherein m can be 0 or 1. L can be $C_xH_{2x}$, wherein x can be 0, 1, 2, 3, 4, or 5, and wherein Y can be $C_{1-6}$ alkylamino, $C_{1-6}$ alkylammonium, or optionally substituted morpholino. $R^1$, $R^2$ and $R^7$-$R^{11}$ can independently be H, or any substituent described herein.

Some embodiments include an ophthalmic liquid comprising a compound described herein and one or more pharmaceutically acceptable excipient.

Some embodiments include a solid dosage form comprising a compound described herein and one or more pharmaceutically acceptable excipients.

Some embodiments include a method of reducing intraocular pressure comprising administering a compound described herein.

Some embodiments include a method or growing hair comprising administering a compound described herein.

DETAILED DESCRIPTION

Certain eicosanoids and their derivatives can be used in glaucoma management. Eicosanoids and derivatives include numerous biologically important compounds such as prostaglandins and their derivatives. Prostaglandins can be described as derivatives of prostanoic acid. Prostanoic acid has the following structural formula:

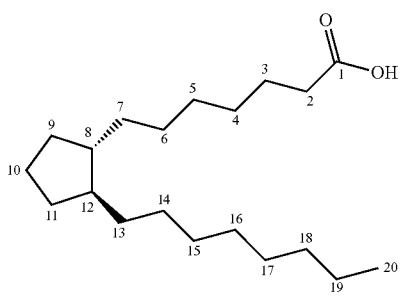

Various types of prostaglandins are classified by the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\alpha}$)]. Changes in the substituents of carbons 9, 10, and 11 can often influence the activity and selectivity of these compounds at the different prostaglandin receptors. Other compounds having more remote structures from natural prostaglandins can also have activity at prostaglandin receptors.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that replaces one or more hydrogen atoms in a parent compound or structural feature. The term "replaces" is merely used herein for convenience, and does not require that the compound be formed by replacing one atom with another. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. A substituent should be sufficiently stable for a compound to be useful for the uses recited herein.

Examples of substituents include, but are not limited to, hydrocarbyl, such as alkyl, alkenyl, alkynyl; heteroalkyl, including any alkyl wherein one or more heteroatoms replaces: one or more carbon atoms and possibly some hydrogen atoms accompanying the carbon atoms (e.g. N replaces CH, O replaces $CH_2$, Cl replaces $CH_3$, etc.), such as alkoxy, alkylthio, haloalkyl, haloalkoxy, amino, etc.; heteroalkenyl, including any alkenyl wherein one or more heteroatoms replaces: one or more carbon atoms and possibly some hydrogen atoms accompanying the carbon atoms, such as acyl, acyloxy, thiocarbonyl, alkylcarboxylate, O-carbamyl, N-carbamyl, O-thiocarbamyl, N-thiocarbamyl, C-amido, N-amido, sulfinyl, isocyanato, isothiocyanato, etc; heteroalkynyl, including any alkynyl wherein one or more heteroatoms replaces: one or more carbon atoms and possibly some hydrogen atoms accompanying the carbon atoms, such as cyano, thiocyanato, cyanato; aryl; heteroaryl; hydroxy; aryloxy; thiol; halo; S-sulfonamido; N-sulfonamido; nitro, silyl; sulfonyl; trihalomethanesulfonyl; trihalomethanesulfonamido; etc.

Where substituents are specified as a range, the range encompasses each individual integer value of substituent including the beginning and ending value of the range. For example, the description of a substituent as "$C_1$ to $C_6$ alkyl" (or "$C_1$-$C_6$ alkyl" or "$C_{1-6}$ alkyl") encompasses $C_1$ alkyl, $C_2$ alkyl, $C_3$ alkyl, $C_4$ alkyl, $C_5$ alkyl, and $C_6$ alkyl. Similarly, the description of a value of "n" (e.g. "$(CH_2)_n$") as being "0 to 3" (or "0-3") encompasses values of "n" of 0, 1, 2, and 3. A skilled person will realize upon a reading of the present disclosure that similar considerations apply to other substituents that can be described in terms of a range (e.g. "5 to 10 ring atoms" and "1 to 3 rings").

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by

attachment may occur at any position normally occupied by a hydrogen atom.

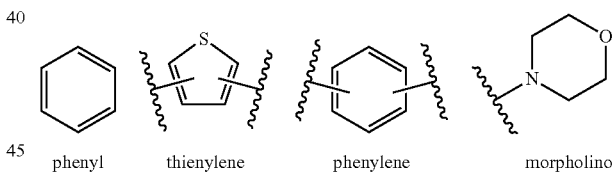

phenyl     thienylene     phenylene     morpholino

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

Certain compound names were generated with ACD version 12.0; and intermediates and reagent names used in the examples were generated with software such as Chem Bio Draw Ultra version 12.0 or Auto Nom 2000 from MDL ISIS Draw 2.5 SP1.

If stereochemistry is not indicated, such as in Formulas 1-12, a name or structural depiction includes any stereoisomer or any mixture of stereoisomers.

With respect to any relevant structural representation, such as Formula 1 or 2, $Ph^1$ is an optionally substituted phenylene. If $Ph^1$ is substituted, it may have 1, 2, 3, or 4 substituents. Any substituent may be included on the phenylene. In some embodiments, some or all of the substituents on the phenylene may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$—O-alkyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2H_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments a substituent of $Ph^1$ is $C_{1-12}$ alkyl, $C_{1-12}$ hydroxyalkyl, F, or Cl. In some embodiments, $Ph^1$ is:

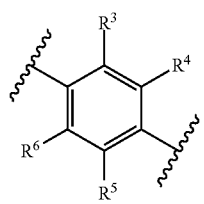

With respect to any relevant structural representation, such as Formula 1, $Ph^2$ is optionally substituted phenyl. If $Ph^2$ is substituted, it may have 1, 2, 3, 4, or 5 substituents. Any substituent may be included on the phenyl. In some embodiments, some or all of the substituents on the phenyl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$—O-alkyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2H_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, a substituent of $Ph^2$ is $C_{1-12}$ alkyl, $C_{1-12}$ hydroxyalkyl, F, or Cl. In some embodiments, $Ph^2$ is:

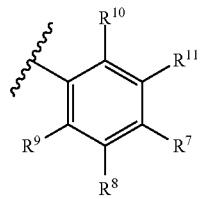

With respect to any relevant structural representation, such as Formula 1, Het is optionally substituted thienylene. If Het is substituted, it may have 1 or 2 substituents. Any substituent may be included on the thienylene. In some embodiments, some or all of the substituents on the thienylene may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may be $C_{1-20}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-20}$—O-alkyl; $C_{1-20}$ hydroxyalkyl; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2H_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, a substituent of Het is $C_{1-4}$ alkyl, F, Cl, OH, CN, or CHO. In some embodiments, Het is:

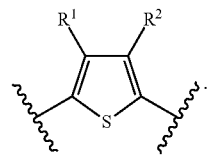

With respect to Formula 1 or 2, in some embodiments, m is 0. In some embodiments, m is 1.

Some compounds may be represented by any of formulas 3-12:

Formula 3

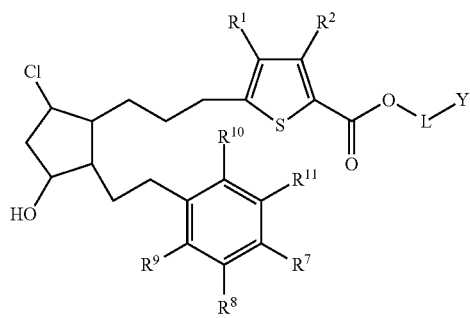

Formula 4
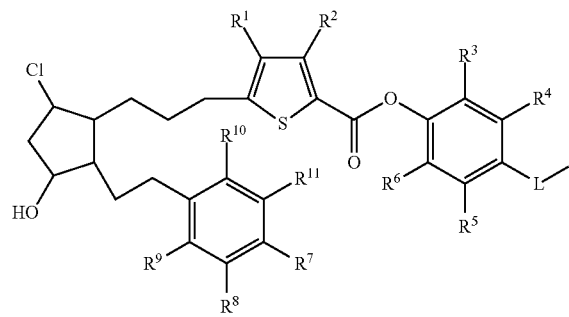

Formula 5
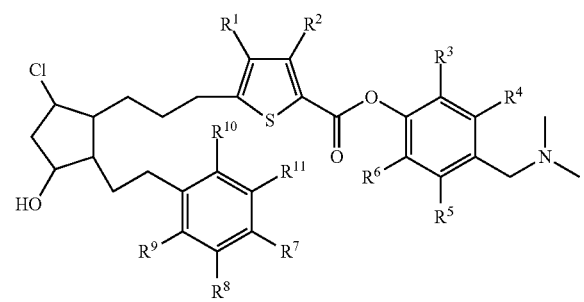

Formula 6
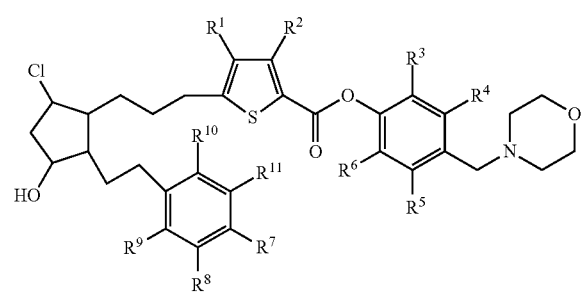

Formula 7
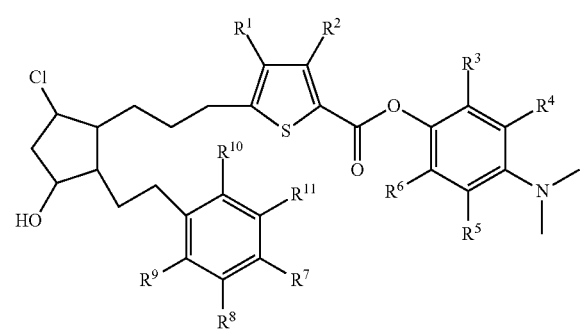

Formula 8
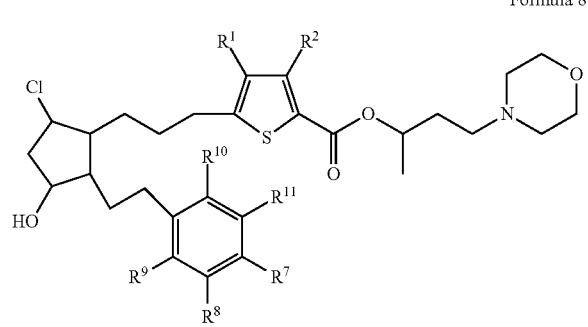

Formula 9
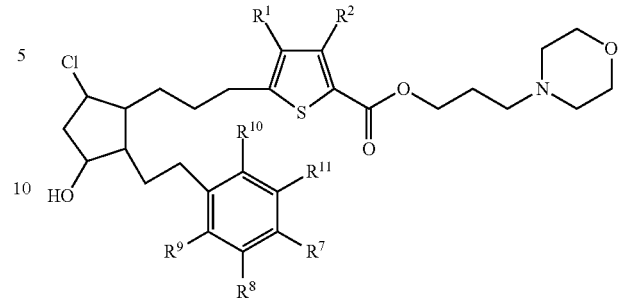

Formula 10
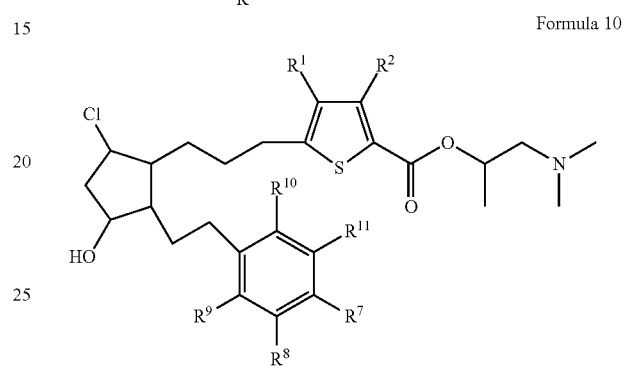

Formula 11
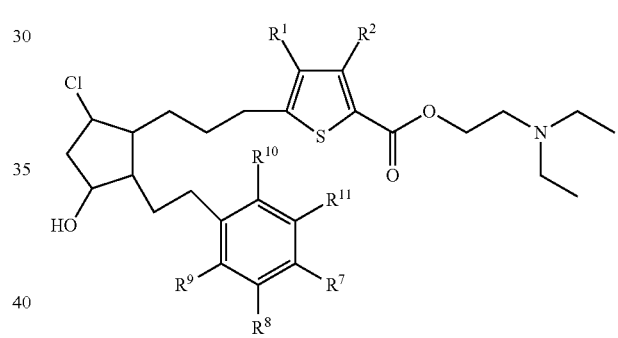

Formula 12
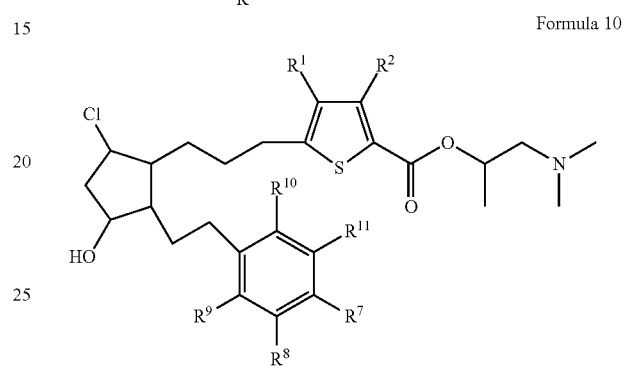

With respect to any relevant structural representation, such as Formula 1 2, or 3, L can be —$C_xH_{2x}$— where x can be 0, 1, 2, 3, 4, or 5. In some embodiments, L is a bond. In some embodiments, L is $CH_2$; $C_2H_4$, such as —$CH_2CH_2$—; $C_3H_6$, such as —$CH_2CH_2CH_2$— or —$CH(CH_3)CH_2$—; or $C_4H_8$, such as —$CH(CH_3)CH_2CH_2$—. In some embodiments, L is a bond. In some embodiments, L is $CH_2$. In some embodiments, L is —$CH_2CH_2$—. In some embodiments, L is —$CH_2CH_2CH_2$—. In some embodiments, L is —$CH(CH_3)CH_2$—. In some embodiments, L is —$CH(CH_3)CH_2CH_2$—.

With respect to any relevant structural representation, such as Formula 1, 2, 3, or 4, Y is $C_{1-6}$ alkylamino, such as $C_{1-6}$ monoalkylamino, $C_{1-6}$ dialkylamino (e.g. dimethylamino, methylethylamino, diethylamino, etc.); $C_{1-6}$ alkylammonium, substituents such as $C_{1-6}$ monalkylammonium, $C_{1-6}$ dialkylammonium, $C_{1-6}$ trialkyl ammonium (e.g. trimethylammonium, methyldiethylammonium, etc.). In some embodiments Y can be:

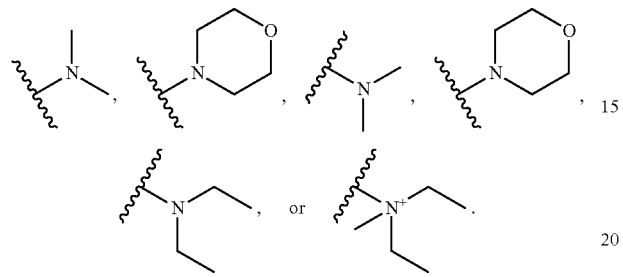

With respect to any relevant structural representation, such as Formula 1, 2, 3, or 4, in some embodiments, Y is

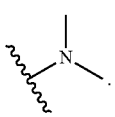

With respect to any relevant structural representation, such as Formula 1, 2, 3, or 4, in some embodiments, Y is

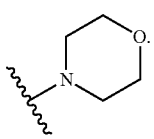 [SMILES: *N1CCOCC1]

With respect to any relevant structural representation, such as Formula 1, 2, 3, or 4, in some embodiments, Y is

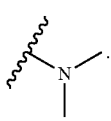 [SMILES: *N(C)C]

With respect to any relevant structural representation, such as Formula 1, 2, 3, or 4, in some embodiments, Y is

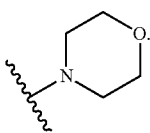 [SMILES: *N1CCOCC1]

With respect to any relevant structural representation, such as Formula 1, 2, 3, or 4, in some embodiments, Y is

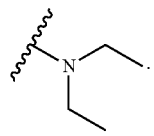 [SMILES: *N(CC)CC]

With respect to any relevant structural representation, such as Formula 1, 2, 3, or 4, in some embodiments, Y is

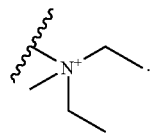 [SMILES: *[N+](C)(CC)CC]

With respect to any relevant structural representation, such as Formula 1-12, $R^1$, $R^2$, $R^3$, $R^4$, $R^5$, $R^6$, $R^7$, $R^8$, $R^9$, $R^{10}$, and $R^{11}$ may independently be H or any substituent, such as a substituent having from 0 to 6 carbon atoms and from 0 to 5 heteroatoms, wherein each heteroatom is independently: O, N, S, F, Cl, Br, or I; and/or having a molecular weight of 15 g/mol to 300 g/mol, or 15 g/mol to 150 g/mol. In some embodiments, $R^1$, $R^2$, $R^3$, $R^4$, $R^5$, $R^6$, $R^7$, $R^8$, $R^9$, $R^{10}$, and $R^{11}$ are independently $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^1$, $R^2$, $R^3$, $R^4$, $R^5$, $R^6$, $R^7$, $R^8$, $R^9$, $R^{10}$, and $R^{11}$ are independently H; F; Cl; CN; $CF_3$; OH; $NH_2$; $C_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.

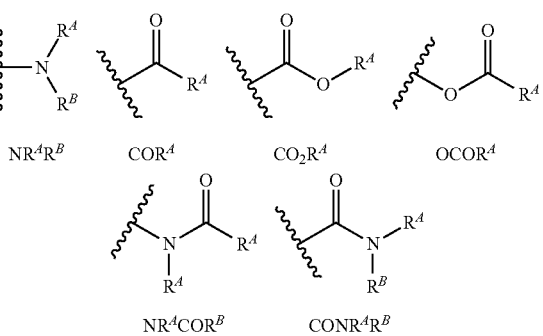

Each $R^A$ may independently be H, or $C_{1-12}$ alkyl, including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

Each $R^B$ may independently be H, or $C_{1-12}$ alkyl, including: linear or branched alkyl having a formula $C_aH_{2a+1}$; or cycloalkyl having a formula $C_aH_{2a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, such as $R^1$-$R^6$, $R^B$ may be H.

With respect to any relevant structural representation, such as Formulas 2-12, $R^1$ is H, or any substituent, such as a substituent having a molecular weight of 15 mol/g to 100 mol/g. In some embodiments $R^1$ is H, $C_{1-6}$ alkyl, or $COCH_3$. In some embodiments, $R^1$ is H. Additionally, for any embodiments above in this paragraph, $R^2$, $R^3$, $R^4$, $R^5$, $R^6$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^1$ is H; $R^2$ can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^2$ is H, or any substituent, such as a substituent having a molecular weight of 15 mol/g to 100 mol/g. In some embodiments, $R^2$ is H, $C_{1-6}$ alkyl, or $COCH_3$. In some embodiments, $R^2$ is H. Additionally, for any embodiments above in this paragraph, $R^1$, $R^3$, $R^4$, $R^5$, $R^6$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments wherein $R^2$ is H; $R^1$ can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 4-7, $R^3$ is H, or any substituent, such as a substituent having a molecular weight of 15 mol/g to 100 mol/g. In some embodiments, $R^3$ is H, $NO_2$, CN, $C_{1-6}$ alkyl, F, Cl, Br or I. In some embodiments, $R^3$ is H. Additionally, for any embodiments above in this paragraph, $R^1$, $R^2$, $R^4$, $R^5$, $R^6$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^3$ is H; $R^4$, $R^5$, and $R^6$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 4-7, $R^4$ is H, or any substituent, such as a substituent having a molecular weight of 15 mol/g to 100 mol/g. In some embodiments, $R^4$ is H, $NO_2$, CN, $C_{1-6}$ alkyl, F, Cl, Br or I. In some embodiments, $R^4$ is H. In some embodiments, $R^4$ is Cl. Additionally, for any embodiments above in this paragraph, $R^1$, $R^2$, $R^3$, $R^5$, $R^6$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments wherein $R^4$ is H; $R^3$, $R^5$, and $R^6$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 4-7, $R^5$ is H, or any substituent, such as a substituent having a molecular weight of 15 mol/g to 100 mol/g. In some embodiments, $R^5$ is H, $NO_2$, CN, $C_{1-6}$ alkyl, F, Cl, Br or I. In some embodiments, $R^5$ is H. In some embodiments, $R^5$ is Cl. Additionally, for any embodiments above in this paragraph, $R^1$, $R^2$, $R^3$, $R^4$, $R^6$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments wherein $R^5$ is H; $R^3$, $R^4$, and $R^6$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 4-7, $R^6$ is H, or any substituent, such as a substituent having a molecular weight of 15 mol/g to 100 mol/g. In some embodiments, $R^6$ is H, $NO_2$, CN, $C_{1-6}$ alkyl, F, Cl, Br or I. In some embodiments, $R^6$ is H. In some embodiments, $R^6$ is Cl. Additionally, for any embodiments above in this paragraph, $R^1$, $R^2$, $R^3$, $R^4$, $R^5$, $R^7$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments wherein $R^6$ is H; $R^3$, $R^4$, and $R^5$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^7$ is H, or any substituent, such as a substituent having a molecular weight of 15 mol/g to 100 mol/g. In some embodiments, $R^7$ is $NO_2$, CN, H, $C_{1-6}$ alkyl, $C_{1-6}$ hydroxyalkyl, F, Cl, Br or I. In some embodiments, $R^7$ is H. Additionally, for any embodiments above in this paragraph, $R^1$, $R^2$, $R^3$, $R^4$, $R^5$, $R^6$, $R^8$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^7$ is H; $R^8$, $R^9$, $R^{10}$, and $R^{11}$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^8$ is H, or any substituent, such as a substituent having a molecular weight of 15 mol/g to 100 mol/g. In some embodiments, $R^8$ is $NO_2$, CN, H, $C_{1-6}$ alkyl, $C_{1-6}$ hydroxyalkyl, F, Cl, Br or I. In some embodiments, $R^8$ is H. In some embodiments, $R^8$ is Cl. Additionally, for any embodiments above in this paragraph, $R^1$, $R^2$, $R^3$, $R^4$, $R^5$, $R^6$, $R^7$, $R^9$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^8$ is H; $R^7$, $R^9$, $R^{10}$, and $R^{11}$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^9$ is H, or any substituent, such as a substituent having a molecular weight of 15 mol/g to 100 mol/g. In some embodiments, $R^9$ is $NO_2$, CN, H, $C_{1-6}$ alkyl, $C_{1-6}$ hydroxyalkyl, F, Cl, Br or I. In some embodiments, $R^9$ is H. Additionally, for any embodiments above in this paragraph, $R^1$, $R^2$, $R^3$, $R^4$, $R^5$, $R^6$, $R^7$, $R^8$, $R^{10}$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^9$ is H; $R^7$, $R^8$, $R^{10}$, and $R^{11}$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^{10}$ is H, or any substituent, such as a substituent having a molecular weight of 15 mol/g to 100 mol/g. In some embodiments, $R^{10}$ is $NO_2$, CN, H, $C_{1-6}$ alkyl, $C_{1-6}$ hydroxyalkyl, F, Cl, Br or I. In some embodiments, $R^{10}$ is H. Additionally, for any embodiments above in this paragraph, $R^1$, $R^2$, $R^3$, $R^4$, $R^5$, $R^6$, $R^7$, $R^8$, $R^9$, or $R^{11}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^{10}$ is H; $R^7$, $R^8$, $R^9$, and $R^{11}$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 2-12, $R^{11}$ is H, or any substituent, such as a substituent having a molecular weight of 15 mol/g to 100 mol/g. In some embodiments, $R^{11}$ is $NO_2$, CN, H, $C_{1-6}$ alkyl, $C_{1-6}$ hydroxyalkyl, F, Cl, Br or I. In some embodiments, $R^{11}$ is H. In some embodiments, $R^{11}$ is Cl. Additionally, for any embodiments above in this paragraph, $R^1$, $R^2$, $R^3$, $R^4$, $R^5$, $R^6$, $R^7$, $R^8$, $R^9$, or $R^{10}$, can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy. In some embodiments, wherein $R^{11}$ is H; $R^7$, $R^8$, $R^9$, and $R^{10}$, can independently be H, $C_{1-4}$ alkyl, OH, $C_{1-4}$—O-alkyl, —CHO, $C_{2-4}$—CO-alkyl, $C_{2-4}$—CO-alkyl, $CO_2H$, $C_{2-4}$—$CO_2$-alkyl, F, Cl, Br, I, $NO_2$, or CN.

With respect to any relevant structural representation, such as Formulas 1-12, in some embodiments $R^8$ and $R^{11}$ are Cl. In some embodiments, $R^7$ and $R^9$ are H. In some embodiments, $R^8$ and $R^{11}$ are H. In some embodiments, $R^7$, $R^9$, and $R^{10}$ are H. Additionally, for any embodiments recited in this paragraph, $R^7$, $R^8$, and $R^9$ can independently be: $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$; or H, F, Cl, CN, $CF_3$, OH, $NH_2$, $C_{1-6}$ alkyl, or $C_{1-6}$ alkoxy.

Some embodiments include optionally substituted 4-((dimethylamino)methyl)phenyl 5-(3-(5-chloro-2-(3,5-dichlorophenethyl)-3-hydroxycyclopentyl)propyl)thiophene-2-carboxylate; optionally substituted 4-(morpholinomethyl)phenyl 5-(3-(5-chloro-2-(3,5-dichlorophenethyl)-3-hydroxycyclopentyl)propyl)thiophene-2-carboxylate; optionally substituted 4-(dimethylamino)phenyl 5-(3-(5-chloro-2-(3,5-dichlorophenethyl)-3-hydroxycyclopentyl)propyl)thiophene-2-carboxylate; optionally substituted 4-morpholinobutan-2-yl 5-(3-(5-chloro-2-(3,5-dichlorophenethyl)-3-hydroxycyclopentyl)propyl)thiophene-2-carboxylate; optionally substituted 3-morpholinopropyl 5-(3-(5-chloro-2-(3,5-dichlorophenethyl)-3-hydroxycyclopentyl)propyl)thiophene-2-carboxylate; optionally substituted 1-(dimethylamino)propan-2-yl 5-(3-(5-chloro-2-(3,5-dichlorophenethyl)-3-hydroxycyclopentyl)propyl)thiophene-2-carboxylate; optionally substituted 2-(diethylamino)ethyl 5-(3-(5-chloro-2-(3,5-dichlorophenethyl)-3-hydroxycyclopentyl)propyl)thiophene-2-carboxylate; or optionally substituted 3-((5-(3-(5-chloro-2-(3,5-dichlorophenethyl)-3-hydroxycyclopentyl)propyl)thiophene-2-carbonyl)oxy)-N,N-diethyl-N-methylpropan-1-aminium.

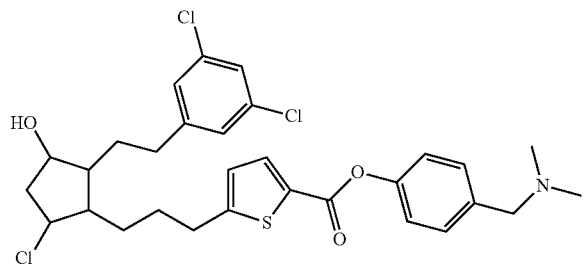 [SMILES: CN(C)Cc1ccc(OC(=O)c2ccc(CCCC3C(Cl)CC(O)C3CCc3cc(Cl)cc(Cl)c3)s2)cc1]

4-((dimethylamino)methyl)phenyl 5-(3-(5-chloro-2-(3,5-dichlorophenethyl)-3-hydroxycyclopentyl)propyl)thiophene-2-carboxylate

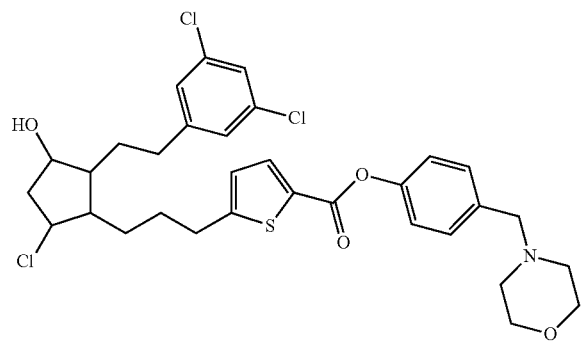 [SMILES: O=C(Oc1ccc(CN2CCOCC2)cc1)c1ccc(CCCC2C(Cl)CC(O)C2CCc2cc(Cl)cc(Cl)c2)s1]

4-(morpholinomethyl)phenyl 5-(3-(5-chloro-2-(3,5-dichlorophenethyl)-3-hydroxycyclopentyl)propyl)thiophene-2-carboxylate

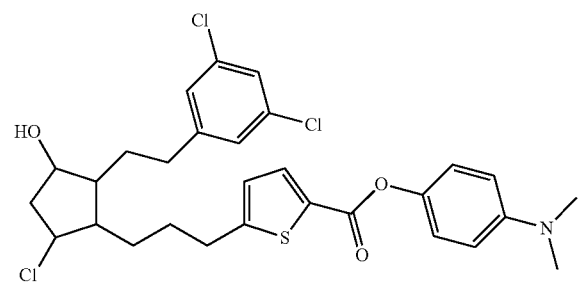 [SMILES: CN(C)c1ccc(OC(=O)c2ccc(CCCC3C(Cl)CC(O)C3CCc3cc(Cl)cc(Cl)c3)s2)cc1]

4-(dimethylamino)phenyl 5-(3-(5-chloro-2-(3,5-dichlorophenethyl)-3-hydroxycyclopentyl)propyl)thiophene-2-carboxylate

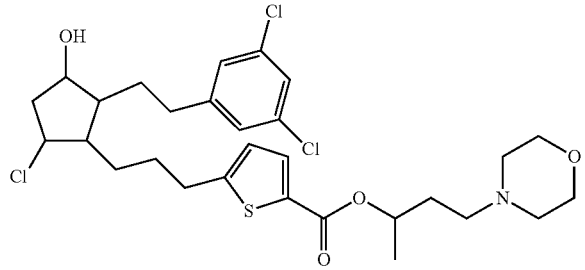 [SMILES: CC(CCN1CCOCC1)OC(=O)c1ccc(CCCC2C(Cl)CC(O)C2CCc2cc(Cl)cc(Cl)c2)s1]

4-morpholinobutan-2-yl 5-(3-(5-chloro-2-(3,5-dichlorophenethyl)-3-hydroxycyclopentyl)propyl)thiophene-2-carboxylate

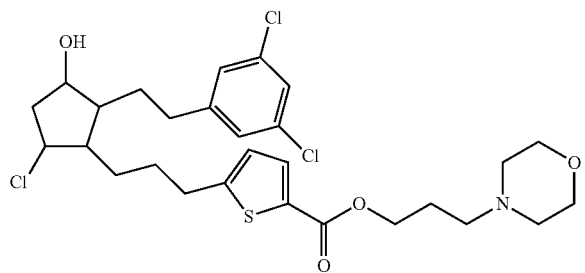 [SMILES: O=C(OCCCN1CCOCC1)c1ccc(CCCC2C(Cl)CC(O)C2CCc2cc(Cl)cc(Cl)c2)s1]

3-morpholinopropyl 5-(3-(5-chloro-2-(3,5-dichlorophenethyl)-3-hydroxycyclopentyl)propyl)thiophene-2-carboxylate

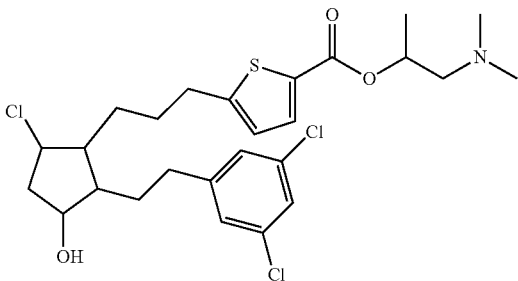 [SMILES: CC(CN(C)C)OC(=O)c1ccc(CCCC2C(Cl)CC(O)C2CCc2cc(Cl)cc(Cl)c2)s1]

1-(dimethylamino)propan-2-yl 5-(3-(5-chloro-2-(3,5-dichlorophenethyl)-3-hydroxycyclopentyl)propyl)thiophene-2-carboxylate

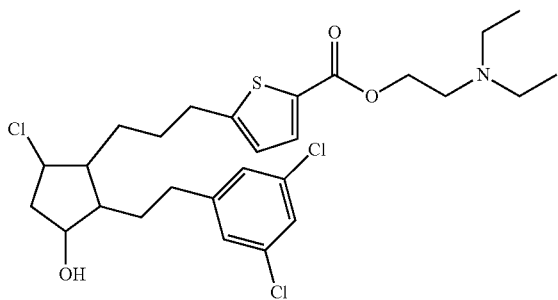 [SMILES: CCN(CC)CCOC(=O)c1ccc(CCCC2C(Cl)CC(O)C2CCc2cc(Cl)cc(Cl)c2)s1]

2-(diethylamino)ethyl 5-(3-(5-chloro-2-(3,5-dichlorophenethyl)-3-hydroxycyclopentyl)propyl)thiophene-2-carboxylate and

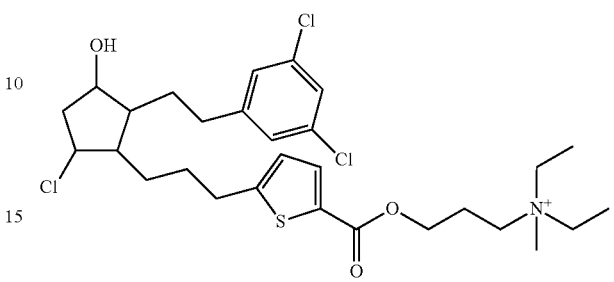

3-((5-(3-(5-chloro-2-(3,5-dichlorophenethyl)-3-hydroxycyclopentyl)propyl)thiophene-2-carbonyl)oxy)-N,N-diethyl-N-methylpropan-1-aminium A compound according to any of Formulas 1-12, optionally substituted 4-((dimethylamino)methyl)phenyl 5-(3-(5-chloro-2-(3,5-dichlorophenethyl)-3-hydroxycyclopentyl)propyl)thiophene-2-carboxylate; optionally substituted 4-(morpholinomethyl)phenyl 5-(3-(5-chloro-2-(3,5-dichlorophenethyl)-3-hydroxycyclopentyl)propyl)thiophene-2-carboxylate; optionally substituted 4-(dimethylamino)phenyl 5-(3-(5-chloro-2-(3,5-dichlorophenethyl)-3-hydroxycyclopentyl)propyl)thiophene-2-carboxylate; optionally substituted 4-morpholinobutan-2-yl 5-(3-(5-chloro-2-(3,5-dichlorophenethyl)-3-hydroxycyclopentyl)propyl)thiophene-2-carboxylate; optionally substituted 3-morpholinopropyl 5-(3-(5-chloro-2-(3,5-dichlorophenethyl)-3-hydroxycyclopentyl)propyl)thiophene-2-carboxylate; optionally substituted 1-(dimethylamino)propan-2-yl 5-(3-(5-chloro-2-(3,5-dichlorophenethyl)-3-hydroxycyclopentyl)propyl)thiophene-2-carboxylate; optionally substituted 2-(diethylamino)ethyl 5-(3-(5-chloro-2-(3,5-dichlorophenethyl)-3-hydroxycyclopentyl)propyl)thiophene-2-carboxylate; or optionally substituted 3-((5-(3-(5-chloro-2-(3,5-dichlorophenethyl)-3-hydroxycyclopentyl)propyl)thiophene-2-carbonyl)oxy)-N,N-diethyl-N-methylpropan-1-aminium (a "subject compound") can be used for reducing intraocular pressure. Reduction of intraocular pressure has been shown to delay or prevent the onset of glaucoma, such as primary open angle glaucoma, and to delay or prevent further vision loss in patients with primary open angle glaucoma. Thus, subject compounds are also useful for treating glaucoma.

Subject compounds can also be used for growing hair, including one or more of: increasing the number of individual hairs, increasing the length of individual hairs, and increasing the width or thickness of individual hairs. Subject compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

For the purposes of this disclosure, "treat," "treating," or "treatment" includes use of a compound, composition, therapeutically active agent, or drug in the diagnosis, cure, mitigation, treatment, or prevention of disease or other undesirable condition.

A pharmaceutically acceptable salt includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. See, e.g., *Handbook of Pharmaceutical Salts*, P. Heinrich Stahl & Camille G. Wermuth (Eds), Verlag; *Helvetica Chimica Acta-Zürich*, 2002, 329-345.

A prodrug includes a compound which is converted to a therapeutically active compound after administration, such as by hydrolysis of an ester group or some other biologically labile group. Ester prodrugs of the subject compounds are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. Some examples of useful esters can include an alkyl ester, a hydroxyalkyl ester, a morpholinoalkyl ester, an aryl ester, or a heteroaryl ester.

Those skilled in the art will readily understand that for administration or the manufacture of medicaments, subject compounds can be admixed with pharmaceutically acceptable excipients. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Liquid pharmaceutically administrable dosage forms can, for example, comprise a solution or suspension of one or more of the subject compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. The composition of the formulation to be administered, in any event, contains a quantity of one or more of the subject compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day.

A liquid which is ophthalmically acceptable includes a liquid that is formulated such that it can be administered topically to the eye. The comfort can be a consideration, although sometimes formulation considerations (e.g. drug stability) may necessitate less than optimal comfort. In the case that comfort is not ideal, the liquid can be formulated such that the liquid is tolerable to the patient for topical ophthalmic use. Additionally, an ophthalmically acceptable liquid can be packaged for single use, or contain a preservative to prevent contamination over multiple uses.

For ophthalmic application, solutions or medicaments are often prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

In some embodiments the stability of the compound is such that, when stored in an aqueous solution at 25° C. for 7 days or 14 days, at least about 70%, at least about 80%, at least about 90%, at least about 95%, at least about 97%, at least about 99% of the original compound, and up to about 100% of the original compound remains in the solution. In some embodiments, the stability of the compound is such that at least about 70%, at least about 80%, at least about 90%, at least about 95%, at least about 97%, at least about 99% of the original compound, and up to about 100% of original compound remains after 7 days of storage in an aqueous solution at 40° C.

Preservatives that may be used in pharmaceutical compositions include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used in an ophthalmically acceptable liquid. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the an ophthalmically acceptable liquids include, but are not limited to, sodium metabisulfite, sodium thiosulfate, acetylcysteine, butylated hydroxyanisole and butylated hydroxytoluene.

Other excipient components which may be included in ophthalmic preparations are chelating agents. A useful chelating agent is edetate disodium, although other chelating agents may also be used in place or in conjunction with it.

Some ophthalmically acceptable liquid dosage forms include ingredients having the following amounts:

| Ingredient | Amount (% w/v) |
| --- | --- |
| subject compound | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing subject compounds are employed. Topical formulations can include a pharmaceutical carrier, co-solvent, emulsifier, penetration enhancer, preservative system, or emollient.

The actual dose of a subject compound depends on factors such as the specific compound, and on the condition to be treated; the selection of the appropriate dose is well within the skill of the skilled artisan with the benefit of this disclosure.

For treatment of diseases affecting the eye including glaucoma, subject compounds can be administered topically, periocularly, intraocularly, or by any other effective means.

In one embodiment, the subject compounds can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so-called bald person, although there is a noticeable absence of terminal hair, the skin does contain vellus hair, which is a fine colorless hair which may require microscopic examination to determine its presence. This vellus hair is a precursor to terminal hair.

The subject compounds can be used to stimulate, such as the conversion of vellus hair to growth as terminal hair, as well as increasing the rate of growth of terminal hair.

The subject compounds can also be used to stimulate growth of eye lashes. Application of a subject compound to an eye or an eyelid can result in lashes that are longer and have a fuller, denser appearance in the treated eye. The changes in the lashes may be apparent on gross inspection. Possible changes to lashes can include increased length of lashes, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation from the skin surface.

In one embodiment, the subject compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more subject compounds and a dermatologically compatible carrier. Effective amounts of the subject compounds may be determined by one of ordinary skill in the art, but will vary depending on the compound employed, frequency of application and desired result. The subject compound will generally range from about 0.0000001 to about 50% by weight; about 0.001 to about 50% by weight; or about 0.1 to about 30% by weight of the dermatological composition.

In one embodiment, the application of the subject compounds for stimulation of hair growth finds applications in mammalian species, including both humans and animals. In humans, the subject compounds can be applied for example, to the scalp, face beard, head, pubic area, upper lip, eyebrows, and eyelids. In animal raised for their pelts, e.g., mink, the subject compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed with respect to hair growth relates to the use of a subject compound incorporated in a suitable pharmaceutical carrier, and applied at the site of thinning hair or baldness for exertion of local action. Accordingly, such topical compositions include those pharmaceutical forms in which the subject compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the subject compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, at least three months, or at least six months.

For topical use on the eyelids or eyebrows, the subject compounds can be formulated in aqueous solutions, creams, ointments, or oils exhibiting physiologically acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matrices may also be employed as well as soluble and insoluble ocular inserts, for instance, based on substances forming in situ gels. Depending on the actual formation and compound to be used, various amounts of the drug and different dose regimens may be employed. Typically, the daily amount of subject compound for treatment of the eyelid may be about 0.1 ng to about 100 mg per eyelid.

For topical use on the skin and scalp, the subject compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betaine, chlorhexidine, benzalkonium chloride, and the like. Various matrices for the slow release delivery may also be used. Typically, the dose to be applied on the scalp is in the range of about 0.1 ng to about 100 mg per day, about 1 ng to about 10 mg per day, or about 10 ng to about 1 mg per day depending on the subject compound and the formulation. To achieve the daily amount of medication depending on the formulation, the subject compound may be administered once or several times daily with or without antioxidants.

EXAMPLES

The following examples are intended only to illustrate the present disclosure and should in no way be construed as limiting the present disclosure.

Example 1

5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-dimethylaminomethyl phenyl ester (2)

To a solution of 5-(3-((1R,2R,3R,5R)-5-chloro-2-(3,5-dichlorophenethyl)-3-hydroxycyclopentyl)propyl)thiophene-2-carboxylic acid, abbreviated as acid 1 (40 mg, 0.087 mmol), 4-dimethylaminopyridine (36.1 mg, 0.296 mmol) and 4-dimethylaminomethyl phenol (26.3 mg, 0.174 mmol) in acetone (2.0 ml) was added N,N'-dicyclohexylcarbodiimide (19.8 mg, 0.096 mmol) and the reaction mixture was stirred at room temperature for 16 hours. The precipitated urea was filtered off and the filtrate was concentrated in vacuo. The residue was taken up in EtOAc, washed with water, saturated aqueous NaCl, dried over MgSO$_4$, filtered, and concentrated. Elution through a flash column (silica gel 60, 230-400 mesh, 5% triethylamine in acetone) gave ester 2 (23.8 mg, 46%) as a viscous oil.

Example 2

5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-morpholin-4-ylmethyl phenyl ester (3)

To a solution of acid 1 (30 mg, 0.064 mmol), 4-dimethylaminopyridine (26.3 mg, 0.215 mmol) and 4-morpholin-4-ylmethyl phenol (24.7 mg, 0.128 mmol) in acetone (2.0 ml) was added N,N'-dicyclohexylcarbodiimide (14.4 mg, 0.070 mmol) and the reaction mixture was stirred at room temperature for 24 hours. The precipitated urea was filtered off and the filtrate was concentrated in vacuo. The residue was taken up in EtOAc, washed with water, saturated aqueous NaCl, dried over MgSO$_4$, filtered, and concentrated in vacuo. Elution through a flash column (silica gel 60, 230-400 mesh, EtOAc) gave ester 3 (20.7 mg, 51%) as a viscous oil.

Example 3

5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-dimethylaminophenyl ester (4)

To a solution of acid 1 (160 mg, 0.34 mmol), 4-dimethylaminopyridine (141 mg, 1.156 mmol) and 4-dimethylaminophenol (93.2 mg, 0.68 mmol) in acetone (8.0 ml) was added N, N'-dicyclohexylcarbodiimide (77.2 mg, 0.374 mmol) and the reaction mixture was stirred at room temperature for 24 hours. The precipitated urea was filtered off and the filtrate was concentrated in vacuo. The residue was taken up in EtOAc, washed with water, saturated aqueous NaCl, dried over MgSO$_4$, filtered, and concentrated in vacuo. Elution through a flash column (silica gel 60, 230-400 mesh, 3% EtOAc in dichloromethane) gave ester 4 (55.4 mg, 28%) as an orange oil.

Example 4

5-(3-{(1R, 2R, 3R, 5R)-5-Chloro-2-[2-(3,5-dichlorophenyl)ethyl]-3-hydroxycyclopentyl}propyl)thiophene-2-carboxylic acid, 1-methyl-3-morpholin-4-yl propyl ester (5)

To a solution of acid 1 (80 mg, 0.17 mmol), 4-dimethylaminopyridine (23.2 mg, 0.190 mmol), and N-(3-hydroxybutyl)morpholine (271 mg, 1.70 mmol) in DMF (2.0 ml) was added 1-(3-dimethylaminopropyl)-3-ethylcarbodiimide hydrochloride (36.4 mg, 0.190 mmol). The reaction mixture was stirred at ambient temperature for 22 hours and diluted with ethyl acetate. The organic layer was washed with water, saturated aqueous NaCl, dried over MgSO$_4$, filtered, and concentrated in vacuo. The crude product was eluted through a flash column (silica gel 60, 230-400 mesh, EtOAc) to afford ester 5 (38.6 mg, 38%) as a clear oil.

Example 5

5-(3-{(1R, 2R, 3R, 5R)-5-Chloro-2-[2-(3,5-dichlorophenyl)ethyl]-3-hydroxycyclopentyl}propyl)thiophene-2-carboxylic acid, 3-morpholin-4-yl propyl ester (6)

To a solution of acid 1 (60 mg, 0.13 mmol), 4-dimethylaminopyridine (16.7 mg, 0.136 mmol), and 4-(3-hydroxypropyl)morpholine (0.18 ml, 1.30 mmol) in DMF (2.0 ml) was added 1-(3-dimethylaminopropyl)-3-ethylcarbodiimide hydrochloride (27.5 mg, 0.143 mmol). The reaction mixture was stirred at ambient temperature for 18 hours and diluted with ethyl acetate. The organic layer was washed with water, saturated aqueous NaCl, dried over MgSO$_4$, filtered, and concentrated in vacuo. The crude product was eluted through a flash column (silica gel 60, 230-400 mesh, 4% MeOH in EtOAc) to afford ester 6 (59.6 mg, 78%) as a light yellow oil.

Example 6

5-(3-{(1R, 2R, 3R, 5R)-5-Chloro-2-[2-(3,5-dichlorophenyl)ethyl]-3-hydroxycyclopentyl}propyl)thiophene-2-carboxylic acid, 2-dimethylamino-1-methyl ethyl ester (7)

To a solution of acid 1 (80 mg, 0.17 mmol), 4-dimethylaminopyridine (21.8 mg, 0.178 mmol), and 1-dimethylamino-2-propanol (0.21 ml, 1.70 mmol) in DMF (2.0 ml) was added 1-(3-dimethylaminopropyl)-3-ethylcarbodiimide hydrochloride (35.8 mg, 0.187 mmol). The reaction mixture was stirred at ambient temperature for 46 hours and diluted with ethyl acetate. The organic layer was washed with water, saturated aqueous NaCl, dried over MgSO₄, filtered, and concentrated in vacuo. The crude product was eluted through a flash column (silica gel 60, 230-400 mesh, 3% MeOH in EtOAc) to afford ester 7 (23 mg, 25%) as a clear oil.

Example 7

5-(3-{(1R, 2R, 3R, 5R)-5-Chloro-2-[2-(3,5-dichlorophenyl)ethyl]-3-hydroxycyclopentyl}-propyl)thiophene-2-carboxylic acid, 2-diethylaminoethyl ester (8)

To a solution of acid 1 (80 mg, 0.17 mmol), 4-dimethylaminopyridine (22.8 mg, 0.187 mmol), and 2-(diethylamino)ethanol (0.23 ml, 1.70 mmol) in DMF (2.0 ml) was added O-(7-azabenzo-triazol-1-yl)-N,N,N',N'-tetramethyluronium hexafluorophosphate (71.1 mg, 0.187 mmol). The reaction mixture was stirred at ambient temperature for 20 hours and diluted with ethyl acetate. The organic layer was washed with water, saturated aqueous NaCl, dried over MgSO₄, filtered, and concentrated in vacuo. The crude product was eluted through a flash column (silica gel 60, 230-400 mesh, 1% triethylamine in EtOAc) to obtain ester 8 (78.5 mg, 82%) as a clear oil.

Example 8

{3-[5-(3-{(1R, 2R, 3R, 5R)-5-Chloro-2-[2-(3,5-dichlorophenyl)ethyl]-3-hydroxycyclopentyl}-propyl)thiophene-2-carbonyloxy]propyl}diethyl methyl ammonium iodide (9)

To a solution of acid 1 (80 mg, 0.17 mmol), 4-dimethylaminopyridine (22.8 mg, 0.187 mmol), and 3-diethylamino-1-propanol (0.25 ml, 1.70 mmol) in DMF (2.0 ml) was added O-(7-azabenzotriazol-1-yl)-N,N,N',N'-tetramethyluronium hexafluorophosphate (71.1 mg, 0.187 mmol). The reaction mixture was stirred at ambient temperature for 23 hours and diluted with ethyl acetate. The organic layer was washed with water, saturated aqueous NaCl, dried over MgSO₄, filtered, and concentrated in vacuo. The crude product was eluted through a flash column (silica gel 60, 230-400 mesh, acetone) to afford the corresponding diethylaminopropylester (42.7 mg, 44%) as a light yellow oil.

A solution of the above diethylaminopropylester ester (77 mg, 0.13 mmol) in anhydrous THF (5 ml) was treated with iodomethane (1 ml). The reaction vial was sealed and the contents were stirred at room temperature for 65 hours. The solvent was removed in vacuo to obtain a deep red, viscous oil which was washed with diethyl ether and dried under vacuum at room temperature to yield ester 9 (97.6 mg, 105%).

The following Table 1 depicts various embodiments indicating the stability of compounds depicted by their respective structures in the table. The compounds were dissolved in an aqueous solution, and maintained at the indicated temperatures, for 7 to 14 days, as indicated.

TABLE 1

| Compound | 25° C./ 7 days | 25° C./ 14 days | 40° C./ 7 days |
| --- | --- | --- | --- |
| 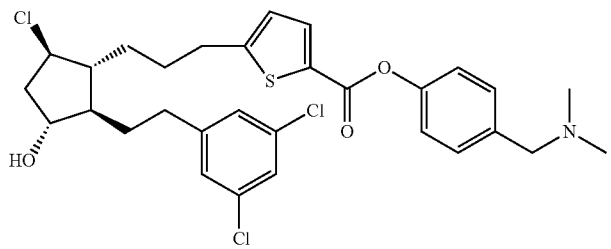 [SMILES: CN(C)Cc1ccc(OC(=O)c2ccc(CCC[C@@H]3[C@@H](CCc4cc(Cl)cc(Cl)c4)[C@H](O)C[C@H]3Cl)s2)cc1] 2 | 96.4 | 95.2 | 78.0 |
| 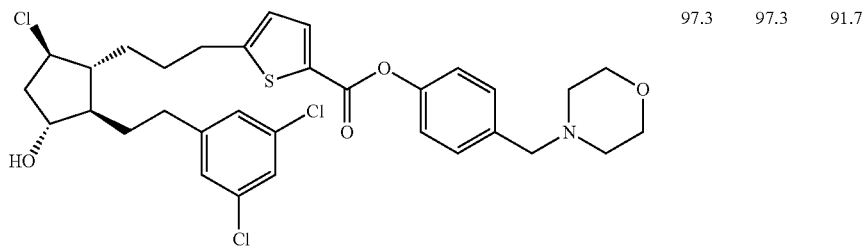 3 | 97.3 | 97.3 | 91.7 |

TABLE 1-continued
| Compound | 25° C./ 7 days | 25° C./ 14 days | 40° C./ 7 days |
|---|---|---|---|
| 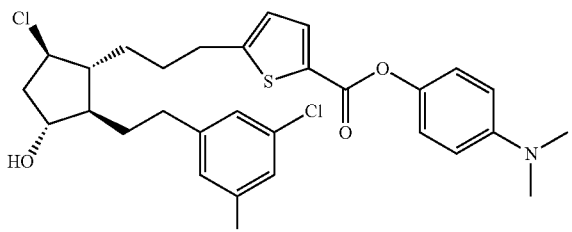 4 | 98.7 | 100.2 | 96.0 |
| 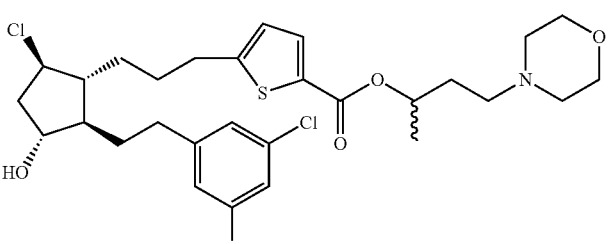 5 | 98.5 | 95.4 | 89.3 |
| 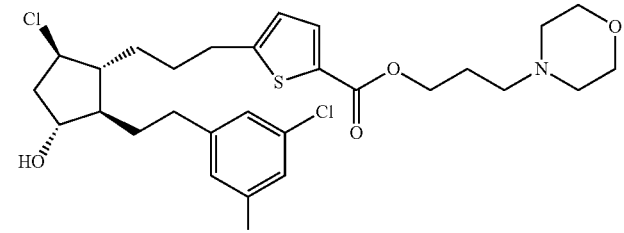 6 | 103.0 | 102.9 | 98.0 |
| 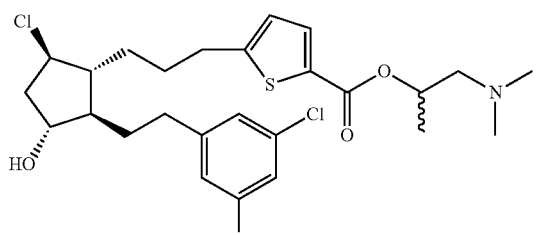 7 | 94.3 | 78.5 | 70.3 |
| 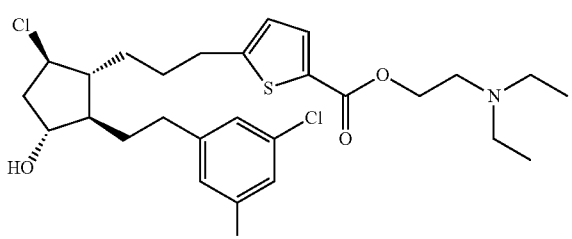 8 | 95.8 | 84.6 | 79.1 |

TABLE 1-continued

| Compound | 25° C./ 7 days | 25° C./ 14 days | 40° C./ 7 days |
|---|---|---|---|
| 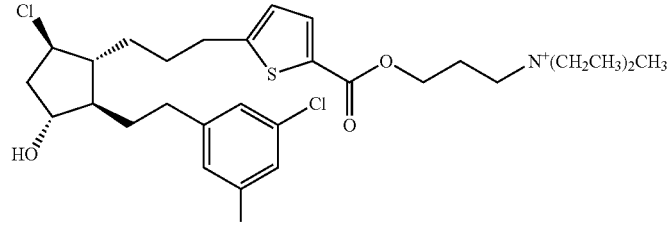 9 | 100.5 | 101.1 | 101.8 |

The following non-limiting embodiments are contemplated:

Embodiment 1

A compound represented by a formula:

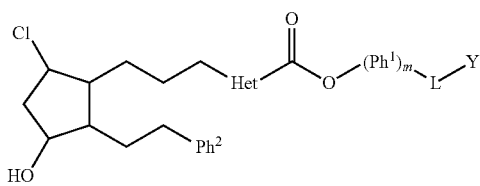

wherein $Ph^1$ is optionally substituted phenylene;
m is 0 or 1;
$Ph^2$ is optionally substituted phenyl;
Het is optionally substituted thienylene;
L is $C_xH_{2x}$, wherein x is 0, 1, 2, 3, 4, or 5;
Y is $C_{1-6}$ alkylamino, $C_{1-6}$ alkylammonium, or optionally substituted morpholino.

Embodiment 2

The compound of embodiment 1, further represented by a formula:

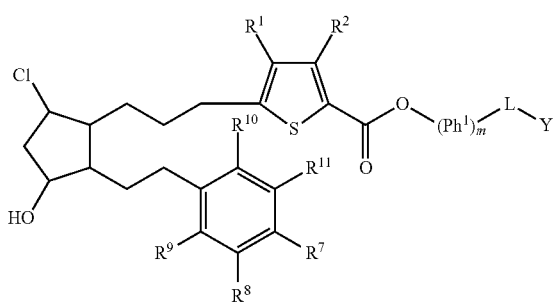

wherein $R^1$, $R^2$, $R^7$, $R^8$, $R^9$, $R^{10}$, and $R^{11}$ are independently H, F, Cl, Br, I, $C_{1-6}$ alkyl, or $C_{1-6}$ hydroxyalkyl.

Embodiment 3

The compound of embodiment 1 or 2, wherein Y is unsubstituted morpholino.

Embodiment 4

The compound of embodiment 1 or 3, wherein Het is unsubstituted thienyl.

Embodiment 5

The compound of embodiment 1, 2, 3, or 4, wherein $Ph^1$ is unsubstituted phenylene.

Embodiment 6

The compound of embodiment 1, 2, 3, 4, or 5, wherein m is 0.

Embodiment 7

The compound of embodiment 1, 2, 3, 4, or 5, wherein m is 1.

Embodiment 8

The compound of embodiment 1, 3, 4, 5, 6, or 7, wherein x is 0.

Embodiment 9

The compound of embodiment 1, 3, 4, 5, 6, or 7, wherein x is 1.

Embodiment 10

The compound of embodiment 1, 3, 4, 5, 6, or 7, wherein x is 2.

Embodiment 11

The compound of embodiment 1, 3, 4, 5, 6, or 7, wherein x is 3.

Embodiment 12

The compound of embodiment 1, 3, 4, 5, 6, or 7, wherein x is 4.

Embodiment 13

The compound of embodiment 1, 2, 3, 4, 5, 6, 7, 8, 9, 10, 11, or 12, wherein Y is $C_{2-4}$ alkylamino.

Embodiment 14

The compound of embodiment 1, 2, 3, 4, 5, 6, 7, 8, 9, 10, 11, or 12, wherein Y is $C_{3-6}$ trialkylammonium.

Embodiment 15

The compound of embodiment 1, 3, 4, 5, 6, 7, 8, 9, 10, 11, 12, 13, or 14, wherein $Ph^2$ is 2,4-dichlorophenyl.

Embodiment 16

The compound of embodiment 2, wherein $R^8$ and $R^{11}$ are Cl.

Embodiment 17

The compound of embodiment 1, 2, 3, 4, 5, 6, 7, 8, 9, 10, 11, 12, 13, 14, 15, or 16, wherein, if substituents are present, each substituent of $Ph^1$, $Ph^1$, and Het has a molecular weight of 15 g/mol to 500 g/mol.

Embodiment 18

An ophthalmic liquid comprising a compound according to embodiment 1, 2, 3, 4, 5, 6, 7, 8, 9, 10, 11, 12, 13, 14, 15, or 16.

Embodiment 19

A solid dosage form comprising a compound according to embodiment 1, 2, 3, 4, 5, 6, 7, 8, 9, 10, 11, 12, 13, 14, 15, or 16.

Embodiment 20

A method of reducing intraocular pressure comprising administering a compound of embodiment 1, 2, 3, 4, 5, 6, 7, 8, 9, 10, 11, 12, 13, 14, 15, or 16 to a mammal in need thereof.

Embodiment 21

A method or growing hair comprising administering a compound of embodiment 1, 2, 3, 4, 5, 6, 7, 8, 9, 10, 11, 12, 13, 14, 15, or 16 to a mammal in need thereof.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of the present disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of any claim. No language in the specification should be construed as indicating any non-claimed element essential to the practice of the compounds, compositions, and methods described herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for making and using the compounds, compositions, and methods described herein. Of course, variations on these described embodiments will become apparent to those of ordinary skill in the art upon reading the foregoing description. It is expected skilled artisans can employ such variations as appropriate, and it is intend for the compounds, compositions, and methods disclosed herein to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed:

1. A compound represented by Formula 1:

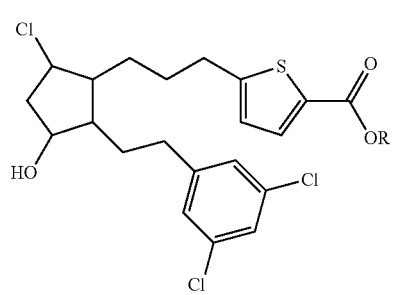

Formula 1 or a pharmaceutically acceptable salt thereof, wherein: R is

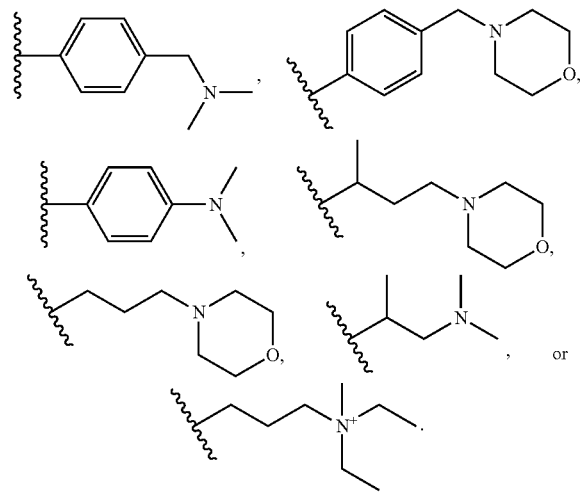

2. The compound of claim 1, wherein the compound is selected from the group consisting of:
- 1-(dimethylamino)propan-2-yl 5-(3-(5-chloro-2-(3,5-dichlorophenethyl)-3-hydroxycyclopentyl)propyl)thiophene-2-carboxylate;
- 3-((5-(3-(5-chloro-2-(3,5-dichlorophenethyl)-3-hydroxycyclopentyl)propyl)thiophene-2-carbonyl)oxy)-N,N-diethyl-N-methylpropan-1-aminium;
- 3-morpholinopropyl 5-(3-(5-chloro-2-(3,5-dichlorophenethyl)-3-hydroxycyclopentyl)propyl)thiophene-2-carboxylate;
- 4-((dimethylamino)methyl)phenyl 5-(3-(5-chloro-2-(3,5-dichlorophenethyl)-3-hydroxycyclopentyl)propyl)thiophene-2-carboxylate;
- 4-(dimethylamino)phenyl 5-(3-(5-chloro-2-(3,5-dichlorophenethyl)-3-hydroxycyclopentyl)propyl)thiophene-2-carboxylate;
- 4-(morpholinomethyl)phenyl 5-(3-(5-chloro-2-(3,5-dichlorophenethyl)-3-hydroxycyclopentyl)propyl)thiophene-2-carboxylate; and
- 4-morpholinobutan-2-yl 5-(3-(5-chloro-2-(3,5-dichlorophenethyl)-3-hydroxycyclopentyl)propyl)thiophene-2-carboxylate;

or a pharmaceutically acceptable salt thereof.

3. The compound of claim 1, wherein the compound is selected from the group consisting of:
- 5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-dimethylaminomethyl phenyl ester;
- 5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-morpholin-4-ylmethyl phenyl ester;
- 5-(3-{(1R, 2R, 3R, 5R)-5-Chloro-2-[2-(3,5-dichlorophenyl)ethyl]-3-hydroxycyclopentyl}-propyl)thiophene-2-carboxylic acid 4-dimethylaminophenyl ester;
- 5-(3-{(1R, 2R, 3R, 5R)-5-Chloro-2-[2-(3,5-dichlorophenyl)ethyl]-3-hydroxycyclopentyl}propyl)thiophene-2-carboxylic acid, 1-methyl-3-morpholin-4-yl propyl ester;
- 5-(3-{(1R, 2R, 3R, 5R)-5-Chloro-2-[2-(3,5-dichlorophenyl)ethyl]-3-hydroxycyclopentyl}propyl)thiophene-2-carboxylic acid, 3-morpholin-4-yl propyl ester;
- 5-(3-{(1R, 2R, 3R, 5R)-5-Chloro-2-[2-(3,5-dichlorophenyl)ethyl]-3-hydroxycyclopentyl}propyl)thiophene-2-carboxylic acid, 2-dimethylamino-1-methyl ethyl ester; and
- {3-[5-(3-{(1R, 2R, 3R, 5R)-5-Chloro-2-[2-(3,5-dichlorophenyl)ethyl]-3-hydroxycyclopentyl}-propyl)thiophene-2-carbonyloxy]propyl}diethyl methyl ammonium iodide;

or a pharmaceutically acceptable salt thereof.

4. An ophthalmic liquid comprising a compound according to claim 1, or a pharmaceutically acceptable salt thereof, and one or more pharmaceutically acceptable excipients.

5. A solid dosage form comprising a compound according to claim 1, or a pharmaceutically acceptable salt thereof, and one or more pharmaceutically acceptable excipients.

6. An ophthalmic liquid comprising a compound according to claim 2, or a pharmaceutically acceptable salt thereof, and one or more pharmaceutically acceptable excipients.

7. A solid dosage form comprising a compound according to claim 2, or a pharmaceutically acceptable salt thereof, and one or more pharmaceutically acceptable excipients.

8. An ophthalmic liquid comprising a compound according to claim 3, or a pharmaceutically acceptable salt thereof, and one or more pharmaceutically acceptable excipients.

9. A solid dosage form comprising a compound according to claim 3, or a pharmaceutically acceptable salt thereof, and one or more pharmaceutically acceptable excipients.

10. A method of reducing intraocular pressure comprising administering a compound of claim 1, or a pharmaceutically acceptable salt thereof, to a mammal in need thereof.

11. A method of growing hair comprising administering a compound of claim 1, or a pharmaceutically acceptable salt thereof, to a mammal in need thereof.

12. A method of reducing intraocular pressure comprising administering a compound of claim 2, or a pharmaceutically acceptable salt thereof, to a mammal in need thereof.

13. A method of growing hair comprising administering a compound of claim 2, or a pharmaceutically acceptable salt thereof, to a mammal in need thereof.

14. A method of reducing intraocular pressure comprising administering a compound of claim 3, or a pharmaceutically acceptable salt thereof, to a mammal in need thereof.

15. A method of growing hair comprising administering a compound of claim 3, or a pharmaceutically acceptable salt thereof, to a mammal in need thereof.

* * * * *